(12) United States Patent
Nguyen et al.

(10) Patent No.: US 11,096,681 B2
(45) Date of Patent: Aug. 24, 2021

(54) ALL-SUTURE SUTURE ANCHOR SYSTEMS AND METHODS

(71) Applicant: CAYENNE MEDICAL, INC., Scottsdale, AZ (US)

(72) Inventors: Hoang P Nguyen, Goodyear, AZ (US); Derek J. Harper, Scottsdale, AZ (US); Kevin N. Baird, Scottsdale, AZ (US)

(73) Assignee: Cayenne Medical, Inc., Scottsdale, AZ (US)

( * ) Notice: Subject to any disclaimer, the term of this patent is extended or adjusted under 35 U.S.C. 154(b) by 438 days.

(21) Appl. No.: 15/938,710

(22) Filed: Mar. 28, 2018

(65) Prior Publication Data
US 2018/0214145 A1    Aug. 2, 2018

Related U.S. Application Data

(63) Continuation of application No. 14/589,960, filed on Jan. 5, 2015, now Pat. No. 9,949,733.
(Continued)

(51) Int. Cl.
*A61B 17/04* (2006.01)
*A61B 17/16* (2006.01)
*A61B 17/06* (2006.01)

(52) U.S. Cl.
CPC .... *A61B 17/0401* (2013.01); *A61B 17/06166* (2013.01); *A61B 17/1615* (2013.01);
(Continued)

(58) Field of Classification Search
CPC ............ A61B 17/0401; A61B 17/0406; A61B 2017/06171; A61B 17/1615; A61B 17/1671
See application file for complete search history.

(56) References Cited

U.S. PATENT DOCUMENTS 7,914,545 B2   3/2011   Ek
9,949,733 B1   4/2018   Nguyen et al.
(Continued)

OTHER PUBLICATIONS

"U.S. Appl. No. 14/589,960, Final Office Action dated Oct. 13, 2017", 13 pgs.
(Continued)

*Primary Examiner* — Olivia C Chang
(74) *Attorney, Agent, or Firm* — Schwegman Lundberg & Woessner, P.A.

(57) ABSTRACT

An all-suture suture anchor system includes an all-suture anchor, an inserter, and a specially designed drill. The drill is used to enlarge the hole and create a pocket under the bone surface from the pre-drilled hole. The created pocket is intended to accommodate the expansion of the anchor when deployed into the bone, generating a true mechanical interference under the bone surface. The anchor is loaded on the inserter and placed at full length vertically inside the drilled hole. While holding the inserter on top of the drilled hole, so that a feature on the inserter keeps the anchor to a desired depth below the bone surface, tension is applied to the suture limb that is connected to the bottom end of the anchor. This tensioning step causes the length of the anchor to contract vertically and the anchor is simultaneously expanded circumferentially to fill the pocket previously created by the drill. Since the pocket created by the drill is intended to contain the deployed anchor, the deployed position of the anchor is consistently predictable.

18 Claims, 8 Drawing Sheets

Related U.S. Application Data

(60) Provisional application No. 61/923,591, filed on Jan. 3, 2014.

(52) U.S. Cl.
CPC .. *A61B 17/1617* (2013.01); *A61B 2017/0406* (2013.01); *A61B 2017/0409* (2013.01)

(56) References Cited

U.S. PATENT DOCUMENTS

| | | | |
|---|---|---|---|
| 2002/0193799 A1* | 12/2002 | Chappuis | A61B 17/1617 606/80 |
| 2004/0153074 A1 | 8/2004 | Bojarski et al. | |
| 2011/0022083 A1 | 1/2011 | Dimatteo et al. | |
| 2011/0022084 A1 | 1/2011 | Sengun et al. | |
| 2012/0109156 A1 | 5/2012 | Overes et al. | |
| 2013/0110165 A1* | 5/2013 | Burkhart | A61B 17/04 606/232 |
| 2013/0123810 A1* | 5/2013 | Brown | A61B 17/0401 606/144 |
| 2015/0250471 A1 | 9/2015 | Nason et al. | |

OTHER PUBLICATIONS

"U.S. Appl. No. 14/589,960, Non Final Office Action dated Jun. 26, 2017", 11 pgs.

"U.S. Appl. No. 14/589,960, Notice of Allowance dated Dec. 27, 2017", 6 pgs.

"U.S. Appl. No. 14/589,960, Response filed Jun. 16, 2017 to Restriction Requirement dated May 15, 2017", 7 pgs.

"U.S. Appl. No. 14/589,960, Response filed Sep. 6, 2017 to Non Final Office Action dated Jun. 26, 2017", 12 pgs.

"U.S. Appl. No. 14/589,960, Response filed Nov. 27, 2017 to Final Office Action dated Oct. 13, 2017", 15 pgs.

"U.S. Appl. No. 14/589,960, Restriction Requirement dated May 17, 2017", 7 pgs.

\* cited by examiner

ALL-SUTURE SUTURE ANCHOR SYSTEMS AND METHODS

This application claims the benefit under 35 U.S.C. 119(e) of the filing date of Provisional U.S. Application Ser. No. 61/923,591, entitled All-Suture Suture Anchor, filed on Jan. 3, 2014, which application is herein expressly incorporated herein by reference, in its entirety.

BACKGROUND OF THE INVENTION

There are many soft-tissue to bone repair procedures, such as rotator cuff, SLAP and Bankart lesion repairs, or reconstruction of labral tissue to the glenoid rim, in which a surgeon needs to secure tissue in close contact with bone by implanting an anchor, pre-loaded with suture, into a hole drilled in the bone at the desired anchor location. Commonly, the anchor which the sutures are attached to is made of either plastic such as PEEK or metal such as Titanium or Stainless Steel. In the case of an implant pulling out of the bone there is a piece of hard material from that implant floating inside the joint space. That piece of material could temporary or permanently be stuck within the joint, causing damage to the articulating surfaces.

Many surgeons are beginning to favor using all-suture suture anchors over traditional suture anchors. One particular advantage of using an all-suture anchor is that it requires a smaller hole to be drilled to the bone. Preserving bone is preferred by surgeons. There are quite a few all-suture anchor designs on the market today intended to capture this trend.

The JuggerKnot™, by Biomet, has its anchor configuration made of a section of #5-polyester suture. The loaded suture is inserted through the length of the #5 suture section of the anchor. The anchor is preloaded on an inserter at the middle point. The inserter pushes the anchor into a drilled hole in the bone until a desired position is reached. The inserter is then removed. Both suture limbs are lightly pulled to contract the anchor, expanding it laterally against the wall of the drilled hole. This design relies on the friction between the suture ball of the anchor and the bone. Depending upon the position inside the hole to which the anchor is deployed or set, anchor slippage may occur when higher tension applied on the anchor until the anchor may move to a harder bone surface such as the cortex.

ConMed Linvatec also has introduced an anchor called the Y-Knot™. The anchor is very much the same construct as the Biomet JuggerKnot anchor in terms of design, but with different suture material. It uses high-strength suture for the anchor instead of polyester suture. The technique for using the anchor is also very similar as the company suggests in its own words: "Drill Pilot Hole, Insert Anchor, and Pull-to set." Since the anchor designs and techniques are similar, the anchor shares the same weakness of relying on friction. Thus, slippage can occur, and pull out strength could not be adequate.

Another similar anchor is from Stryker and is called Iconix™. The anchor is designed to have opening sections along the sheet portion, which claim to provide a bunching effect using targeted compression zones. The middle point of the anchor is also preloaded on an inserter and inserted into a pre-drilled hole. When deployed by applying tension on the pre-loaded suture limbs, instead of the whole section of the anchor expanding randomly within the hole, those opening sections on the anchor are intended to swing outward laterally up to 3 mm-4 mm. However, such claimed expansion dimensions are theoretical only, because the soft suture is not stiff enough to penetrate the hole to achieve such dimensions in practice.

SUMMARY OF THE INVENTION

The following disclosure describes the design for a novel all-suture suture anchor together with the associated delivery accessories and methods which are intended to secure tissue to bone. The all-suture anchor eases this concern and gives surgeons piece of mind, because when an all suture anchor pulls out, there is only a piece of soft suture left in the joint.

This invention is described as a system which consists of a uniquely constructed anchor, and inserter, and a specially designed drill. The drill is used to enlarge the hole and create a pocket under the bone surface from the pre-drilled hole. The created pocket is intended to accommodate the expansion of the anchor when deployed into the bone, generating a true mechanical interference under the bone surface. The anchor is loaded on the inserter and placed at full length vertically inside the drilled hole. While holding the inserter on top of the drilled hole, so that a feature on the inserter keeps the anchor to a desired depth below the bone surface, tension is applied to the suture limb that is connected to the bottom end of the anchor. This tensioning step causes the length of the anchor to contract vertically and the anchor is simultaneously expanded circumferentially to fill the pocket previously created by the drill. Since the pocket created by the drill is intended to contain the deployed anchor, the deployed position of the anchor is consistently predictable. The interference of the deployed anchor underneath the bone surface guarantees superior pull out strength and repeatability.

The invention described is a system that allows a surgeon to create a bone-to-soft tissue repair with an all-suture anchor and at the same time, achieve a pull out strength equivalent to the commonly used plastic or metal screw-in anchor.

More particularly, there is provided an all-suture suture anchoring system, which comprises a suture anchor fabricated entirely of a suture material, including connected suture links forming a length of the suture anchor and a preloaded suture woven through the links, and further comprising a tensioning suture limb extending from one end of the suture anchor. The suture anchoring system further includes an inserter for inserting the suture anchor into a bone hole, the inserter comprising an outer tube, a distal end extending distally from the outer tube, and an internal push rod disposed within said inserter, wherein the distal end includes a chamber for containing the suture anchor therein and is movable proximally to retract telescopically into the outer tube and distally to extend telescopically from the outer tube.

The outer tube further comprises a distal edge for contacting the bone surface and functioning as a stop when the inserter is being inserted into a bone hole. The internal push rod is fixed to the outer tube and housed inside both of the outer tube and the distal end, the internal push rod is configured to extend distally a short distance beyond a distal end of the outer tube. The suture anchor is disposed within the chamber, and a distal end of the internal push rod contacts a proximal end of the suture anchor. When the distal end is retracted proximally into the outer tube, the push rod pushes the suture anchor out of the distal end of the inserter.

The connected links of the suture anchor are each formed by tied alternating half-hitch knots, using two strands of suture material.

The system further includes a drill assembly, comprising an outer sleeve and a cutting blade housed within the outer sleeve. The outer sleeve comprises a window disposed through a portion thereof. The cutting blade is pivotally attached to the outer sleeve, so that the cutting blade may be pivoted between a retracted orientation, wherein it is housed within an outer diameter of the outer sleeve, and an extended orientation, wherein the cutting blade extends outwardly of the outer sleeve, through the window.

The drill assembly further includes an actuator for actuating the cutting blade between its retracted and expanded orientations. The actuator comprises a control rod housed within the outer sleeve and movable axially between proximal and distal positions, so that when the control rod moves distally, an actuating surface on the control rod contacts the cutting blade to cause it to pivot outwardly, and when the control rod moves proximally, the actuating surface ceases contact with the cutting blade so that the blade pivots back into the outer sleeve and its retracted orientation.

In another aspect of the invention, there is provided a drill assembly for forming a hole in bone or another procedural site, for implantation of a bone anchor. The drill assembly comprises an outer sleeve, a cutting blade housed within the outer sleeve, wherein the cutting blade is pivotally attached to the outer sleeve, and an actuator for pivoting the cutting blade between retracted and expanded orientations. The outer sleeve comprises a window disposed through a portion thereof, wherein when the cutting blade is in its retracted orientation, it is housed within an outer diameter of the outer sleeve, and when the cutting blade is in its extended orientation, the cutting blade extends outwardly of the outer sleeve, through the window. The actuator comprises a control rod housed within the outer sleeve and movable axially between proximal and distal positions, so that when the control rod moves distally, an actuating surface on the control rod contacts the cutting blade to cause it to pivot outwardly, and when the control rod moves proximally, the actuating surface ceases contact with the cutting blade so that the blade pivots back into the outer sleeve and its retracted orientation.

In still another aspect of the invention, there is disclosed a method of anchoring soft tissue to a suitable bone site, using an all-suture suture anchor. The method comprises steps of creating a pre-drilled pilot hole having a first diameter, inserting a drill assembly into the pre-drilled hole to a desired depth, moving an actuator to pivot a cutting blade from a retracted position within an outer diameter of an outer sleeve of the drill assembly to an expanded position extending outside of the outer diameter of the outer sleeve, and rotating the outer sleeve (using the drill) to create a pocket in the bone site beneath the pre-drilled pilot hole, the pocket having a second diameter greater than the first diameter. Once the pocket is fully created, the next step is to collapse the cutting blade to its retracted position, and to remove the drill assembly from the bone hole. An anchor inserter is then inserted into the bone hole and pocket, wherein the anchor inserter comprises an outer sleeve housing the all-suture suture anchor, after which the suture anchor is released within the pocket by retracting a distal tip of the anchor inserter. Then, tension is applied to a suture limb extending from the anchor to contract the anchor vertically, thereby causing the anchor to expand horizontally to contact opposing edges defining the pocket, so that the suture anchor is wider than the first diameter.

The invention, together with additional features and advantages thereof, may best be understood by reference to the following description taken in conjunction with the accompanying illustrative drawing.

DETAILED DESCRIPTION OF THE INVENTION

Figure 1:
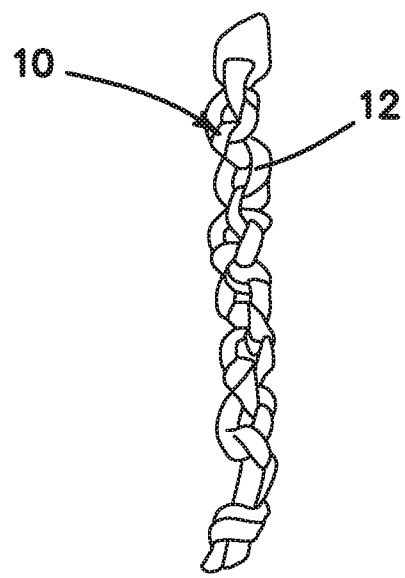
FIG. 1 is a view showing one embodiment of an all-suture anchor construct with eight links, constructed in accordance with the principles of the present invention.
Figure 2:
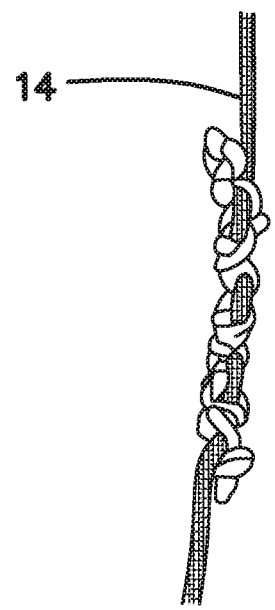
FIGS. 2 and 3 illustrate the anchor construct of FIG. 1, with a preloaded length of suture woven through the loops thereof to make a complete anchor assembly.
Figure 3:
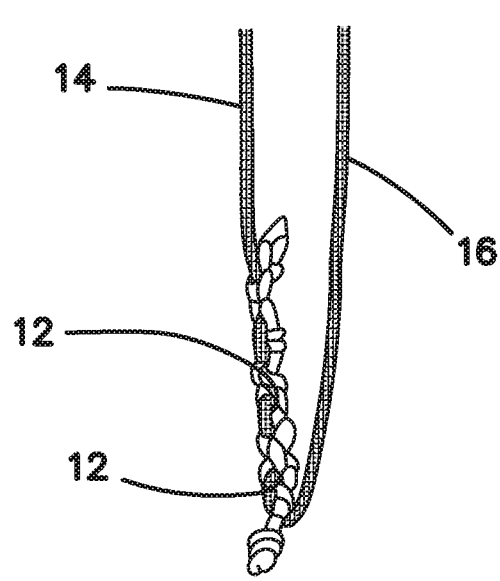

Referring now more particularly to the drawings, there is shown in FIG. 1 a suture anchor 10 comprised entirely of a suture material. In the illustrated embodiment, the anchor 10 includes eight connected suture links 12. The linkage 10, formed of the links 12, is created by tying two alternating half hitches using two strands of #2 high strength suture. The two suture strands continue to form a small loop, then followed by two alternating half hitches. As shown in FIG. 2, a preloaded suture 14 is woven through the links or loops 12 on the anchor 10 to make a complete anchor assembly. As shown in FIG. 3, a tensioning suture limb 16 extends from one end of the anchor 10.

Figure 4:
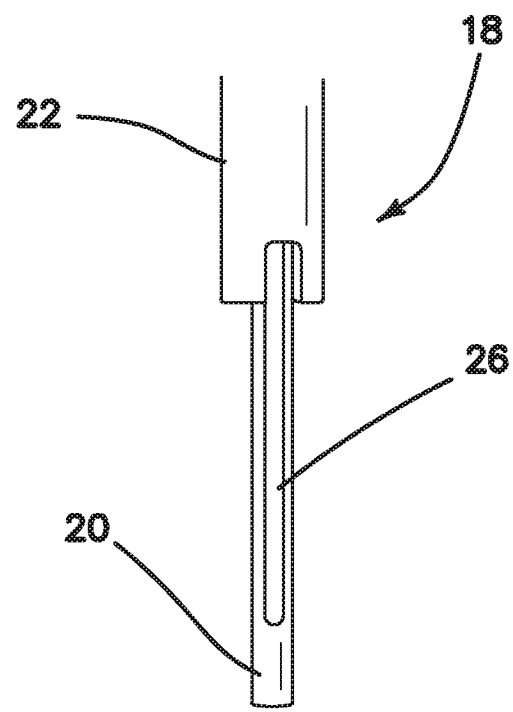
FIG. 4 illustrates a distal end of one embodiment of an inserter constructed in accordance with the principles of the present invention.
Figure 5:
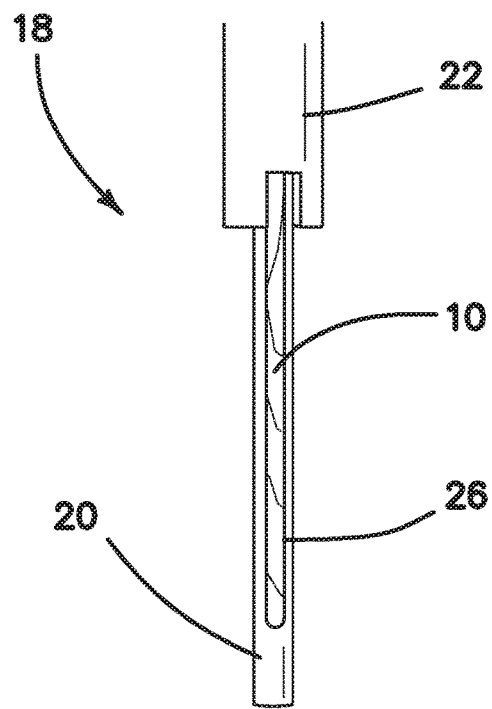
FIG. 5 is a view similar to FIG. 4, wherein the distal end has been loaded with an anchor according to the invention.
Figure 6:
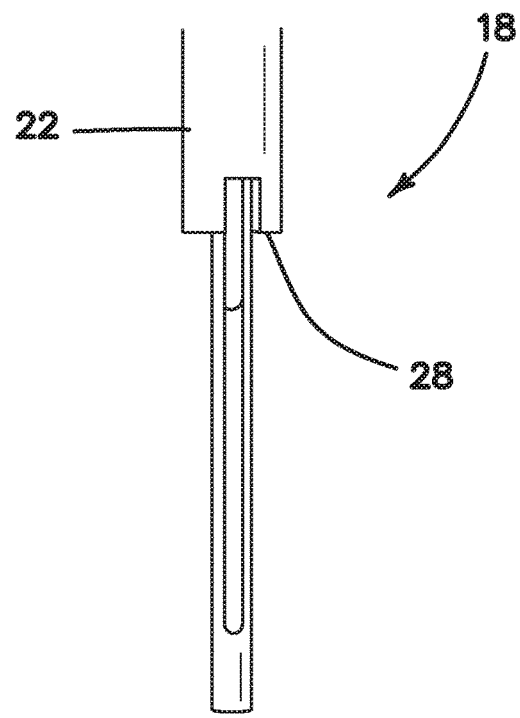
FIG. 6 is a view similar to FIGS. 4-5, showing the distal end in an extended position.
Figure 7:
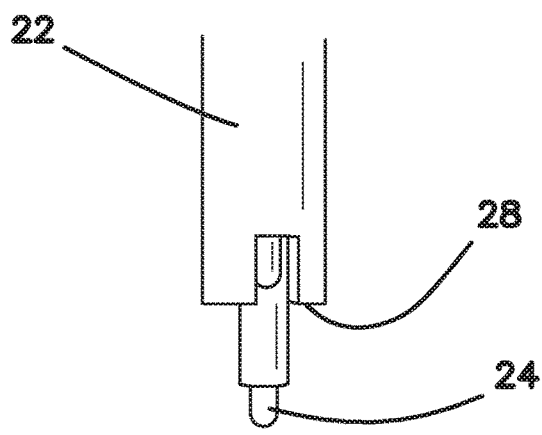
FIG. 7 is a view similar to FIGS. 4-6, wherein the distal end has been retracted proximally into an outer tube of the inserter.
Figure 8:
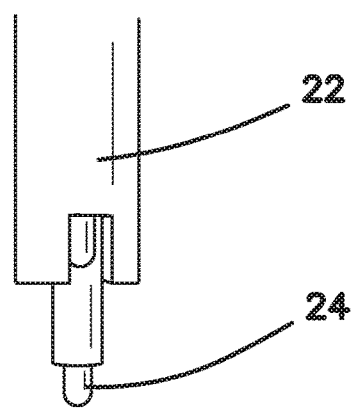
FIG. 8 is a view illustrating a push rod disposed within the inserter, visible with the distal end in its retracted position.
Figure 9:
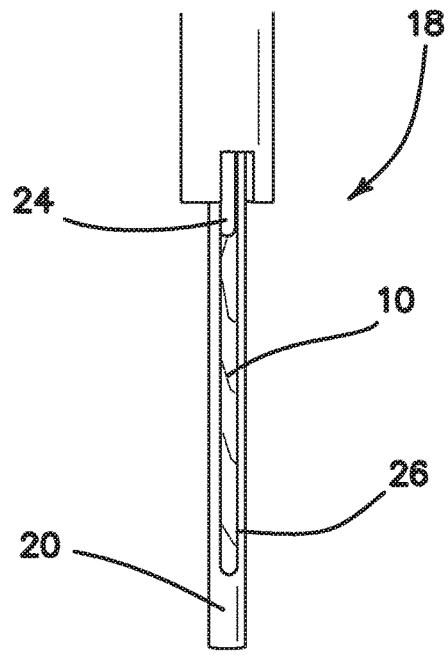
FIG. 9 is a view similar to FIG. 8 illustrating the push feature contacting the preloaded anchor.

Now with reference to FIGS. 4-9, in particular, details of an inserter 18 for use in the inventive system are shown. The inserter 18 comprises three main elements. These elements include an inserter distal end 20 (FIGS. 4 and 5), an outer tube 22 (FIGS. 6-8), and an internal push rod 24 (FIGS. 8 and 9). The distal tip or end 20 houses the anchor 10 (FIG. 5) during insertion into a drilled hole in the bone site. This distal section 20 is constructed, in the illustrated embodiment, of thin wall tubing with a chamber 26 having an internal diameter (ID) that fits the profile and length of the anchor 10, as shown in FIGS. 4 and 5.

The outer tube 22 functions as a telescoping mechanism for the distal end 20 to retract proximally in order to release the anchor 10 from the chamber 26. During insertion into a bone hole, a distal end 28 of the outer tube 22 also stops on the bone surface, indicating to the practitioner that the desired depth has been reached.

The small internal push rod 24 is fixed to the outer tube 22, housed inside both of the distal and the outer tubes 20, 22, respectively, of the inserter 18, and configured to protrude distally a few millimeters from the end of the outer tube 22, as shown in FIG. 8. This built-in feature is adapted to contact the proximal end of the preloaded anchor 10. When the distal end 20 retracts into the outer tube 22, this push rod 24 pushes the anchor 10 out of the distal end of the inserter 18.

A rotating mechanism such as a wheel or a knob is attached to the inserter 18 to help apply enough tension on the preloaded suture limb 16 to completely deploy the anchor. The tensioning suture limb 16 is attached to this mechanism to ensure that tension is always applied on that suture limb.

Figure 10:
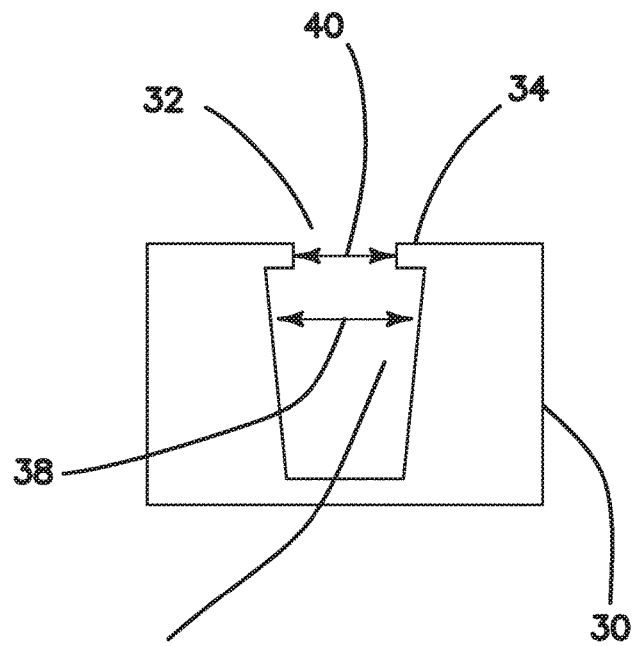
FIG. 10 is a schematic view illustrating a bone site for use in connection with the inventive anchor and drill system.
Figure 11:
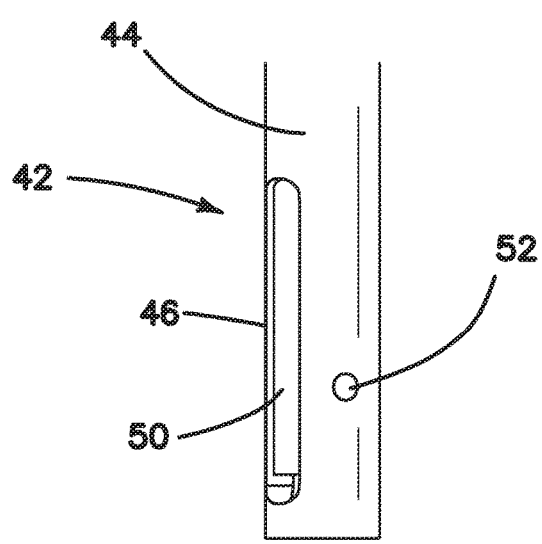
FIG. 11 is a view illustrating one embodiment of a drill assembly according to the invention.

Another aspect of the present invention is the provision of a drill system suitable for creating a bone hole configuration such as that shown in FIG. 10. As illustrated, a procedural site is selected in suitable bone 30. A pre-drilled hole 32 is formed on bone surface 34. The goal of the drilling system is to be able to insert the drill into the pre-drilled hole 32, and to enlarge the hole at a certain depth beneath the bone surface 34 (or cortex) to create a pocket 36. A diameter 38 of the pocket 36 is substantially larger than a diameter 40 of the pre-drilled hole 32, as is evident from FIG. 10.

Figure 12:
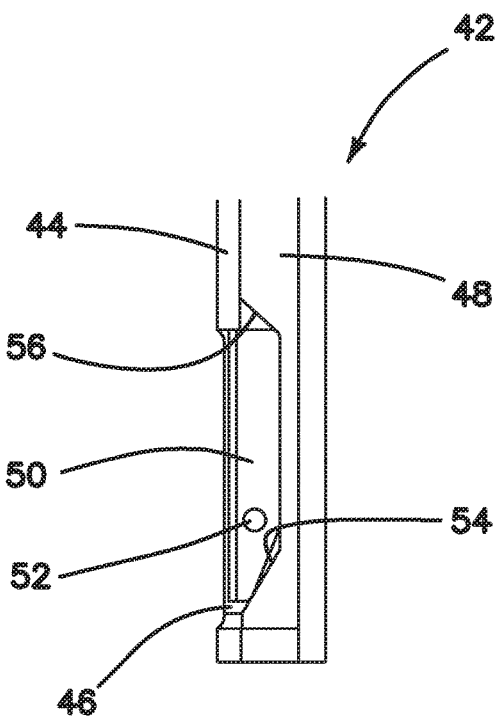
FIG. 12 is a cross-sectional view of the drill assembly of FIG. 11.
Figure 13:
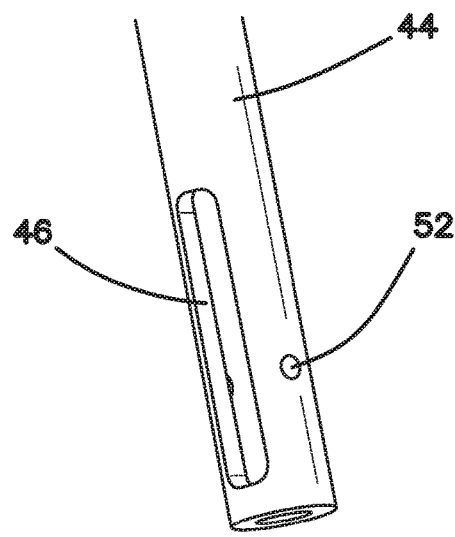
FIG. 13 is a view showing a drill sleeve of the drill assembly of FIGS. 11 and 12.
Figure 14:
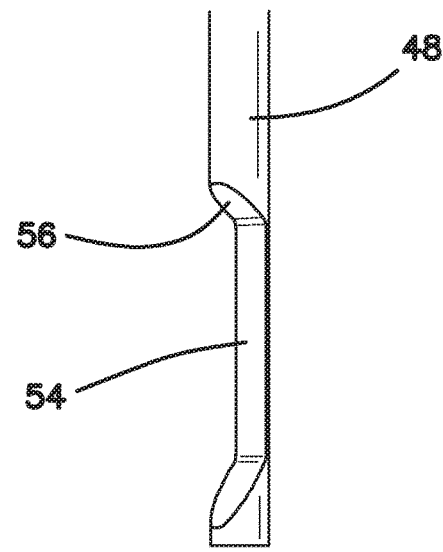
FIG. 14 is a view illustrating an inner control rod of the drill assembly of FIGS. 11 and 12.
Figure 15:
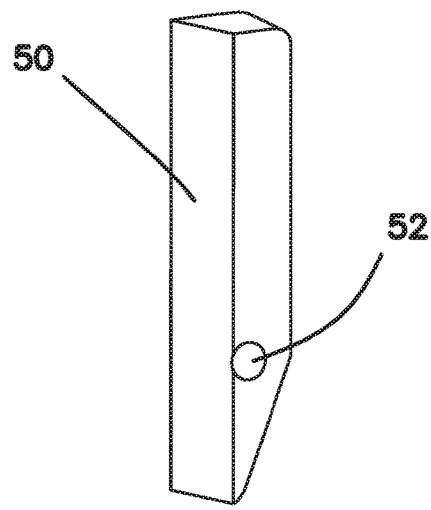
FIG. 15 is a view showing a cutting blade of the drill assembly of FIGS. 11 and 12.
Figure 16:
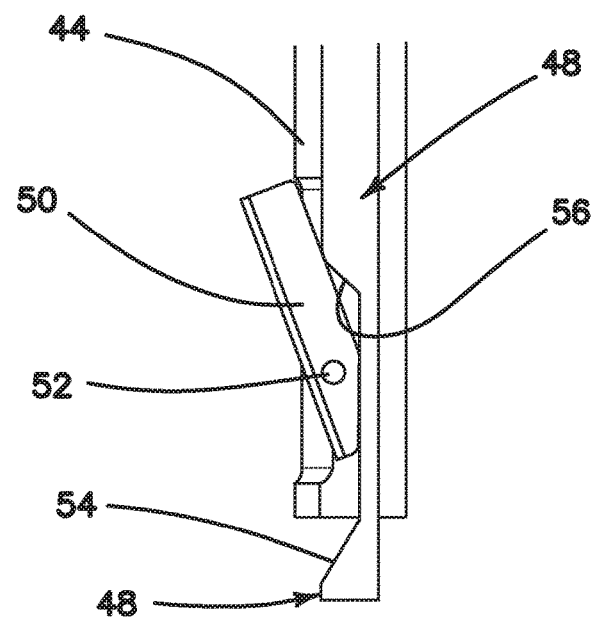
FIG. 16 is a view showing the cutting blade of the drill assembly in a pushed-out extended orientation.
Figure 17:
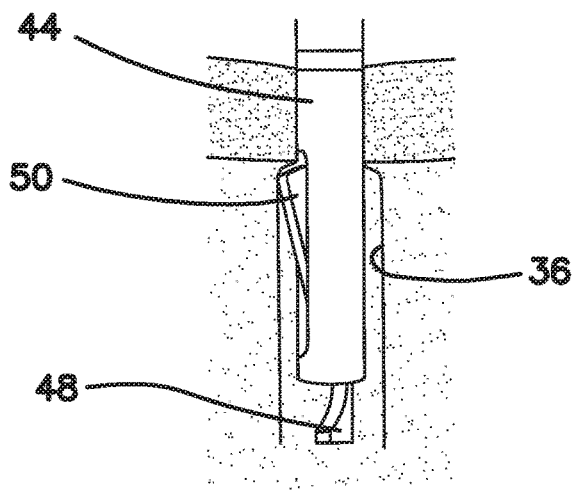
FIG. 17 is a view showing the cutting blade removing bone at a procedural site.
Figure 18:
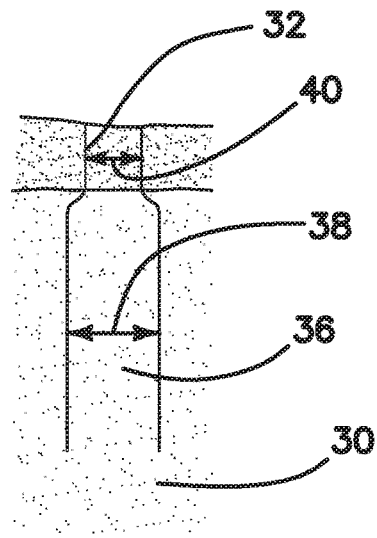
FIG. 18 shows a pocket created below bone surface using the inventive system.

As shown in FIGS. 11-16, the drill assembly 42 of the present invention comprises three main components. These components include an outer sleeve 44 having a cut window 46, an inner control rod 48 and a cutting blade 50. When the control rod 48 is in the position shown in FIG. 12, the cutting blade 50 is secured from pivoting or swinging outwardly through the cut window 46 about a pivot attachment 52, comprising a hole 52 in the outer sleeve 44 and a pin 52 or the like attached to the blade and secured to the outer sleeve through the hole, by means of which the cutting blade 50 is pivotally attached to the outer sleeve 44. Thus, in this orientation, the cutting blade 50 resides within the outer diameter (OD) of the outer sleeve 44, tucked within a suitably sized recess or drill-controlled feature 54 (FIGS. 12, 14, and 16). Since the outer sleeve 44 is of approximately the same diameter as the diameter 40 of the pre-drilled hole 32, it can be inserted into the hole 32. Once inserted to the desired depth, beneath the cortical bone surface 34, the control rod 48 is pushed distally, so that an actuating surface 56 contacts the inside edge of the blade 50 and pushes it outwardly, as shown in FIG. 16, causing it to pivot about the pivot joint 52 to an expanded orientation. FIG. 17 illustrates this orientation, and shows how the blade 50 in its expanded orientation forms the pocket 36. While FIG. 18 illustrates the pocket 36 once formed, with the drill removed.

Figure 19:
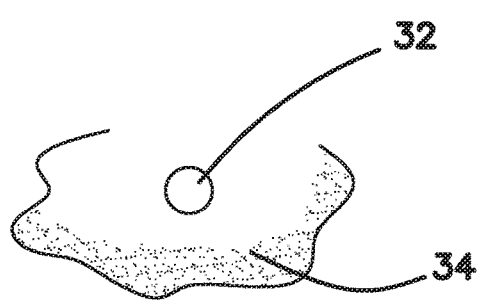
FIG. 19 shows a pre-drilled pilot hole in the bone surface.
Figure 20:
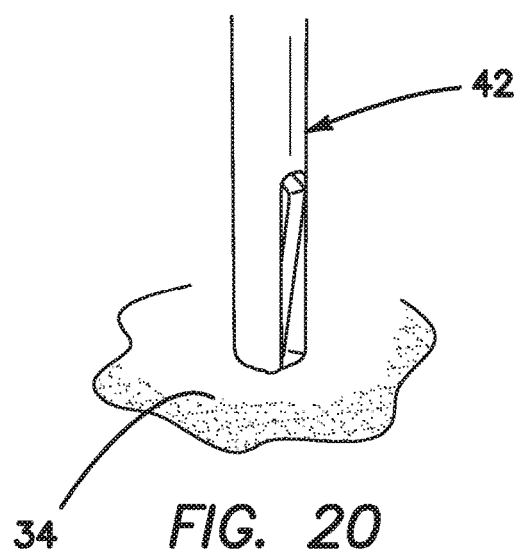
FIG. 20 is a view showing the drill assembly being inserted into the pilot hole of FIG. 19.
Figure 21:
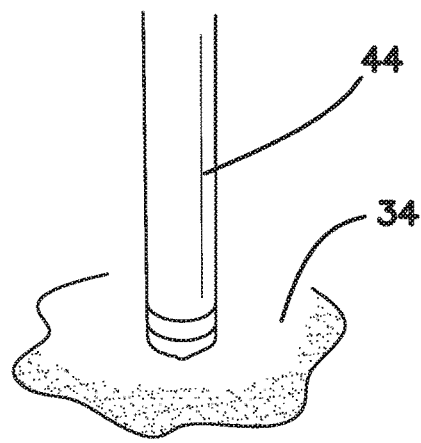
FIG. 21 is a view similar to FIG. 20 wherein the drill has been fully inserted into the pilot hole.
Figure 22:
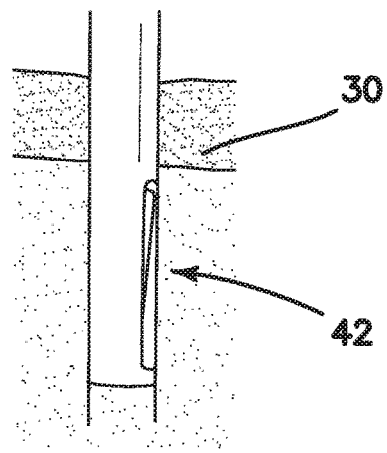
FIG. 22 is a cut-away view showing the drill within the created hole in the bone site.

FIGS. 19-30 illustrate, in sequence, a representative method for using the inventive system to secure an anchor 10 in place. In this representative method; a first step is to create a pre-drilled pilot hole 32 in the cortical bone surface 34 (FIG. 19). The hole 32 is tapped, if necessary. Then, the drill assembly 42 is inserted into the pilot hole 32 (FIGS. 20 and 21), once it is verified that the cutting blade 50 is fully collapsed inside the window 46 on the outer sleeve 44. The distal end is inserted into the hole until a marking 58 on the outer sleeve 44 is level with the bone surface 34, or, alternatively, a drill guide or other visualization or detection approach is used to control the depth (FIG. 22).

Figure 23:
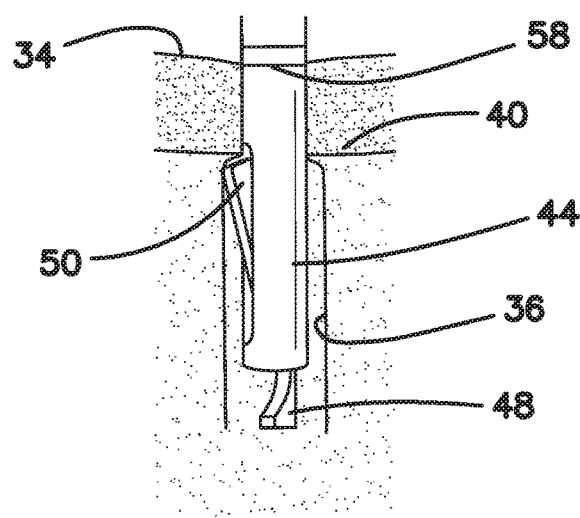
FIG. 23 is a view similar to FIG. 22 showing the cutting blade in its extended orientation.
Figure 24:
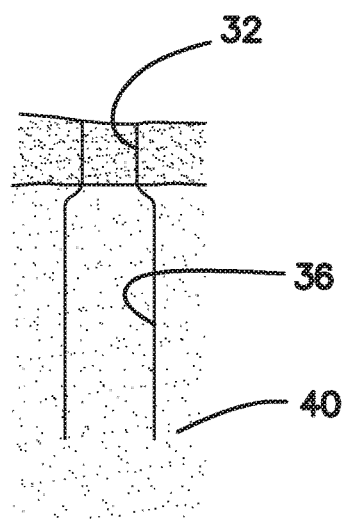
FIG. 24 is a view of the bone hole wherein a pocket has been created.
Figure 25:
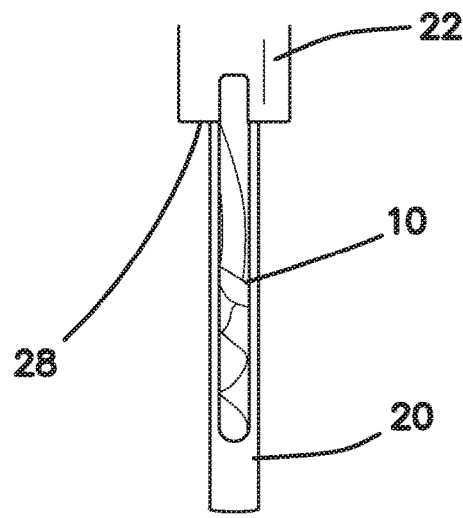
FIG. 25 illustrates the inserter with loaded anchor.

When the predetermined desired depth has been reached, the control rod 48 is pushed distally, as shown in FIG. 23, until it firmly stops, thus pivoting the blade 50 to its fully extended or expanded orientation. At this point, the drill may be activated to rotate the bit and cause the blade 50 to form the pocket 36, as shown in FIGS. 23 and 24. Again, a drill guide can be used to control the depth.

Once the pocket 36 has been fully formed, the control rod 48 is pulled proximally all the way up until it firmly stops to fully collapse the cutting blade 50 into the outer sleeve 44. Then, the drill is removed from the hole (FIG. 24).

Figure 26:
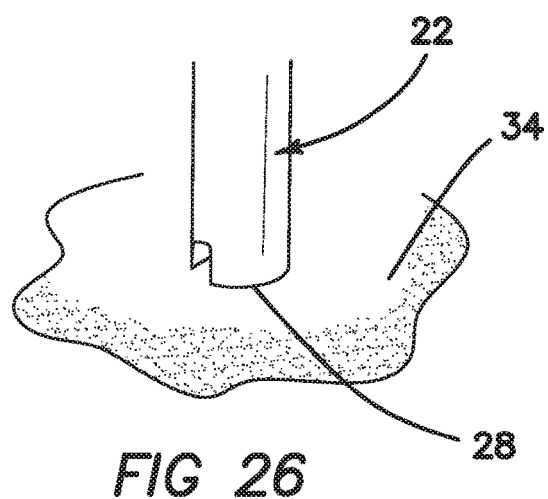
FIG. 26 is a view illustrating the inserter inserted into the bone hole until abutting a stop.
Figure 27:
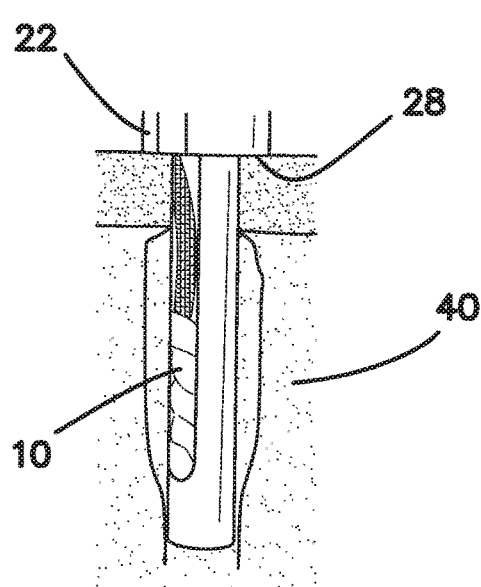
FIG. 27 illustrates the inserter and loaded anchor inside the bone hole.
Figure 28:
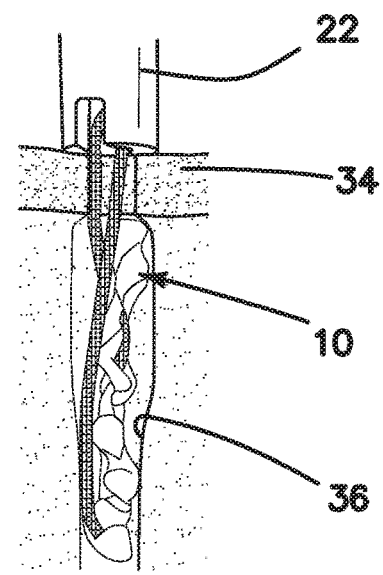
FIG. 28 shows a step of the inventive method wherein the anchor is placed within the created bone hole.

At this point, the inserter tip 20 with loaded anchor 10 (FIG. 25) is inserted into the hole until the distal end 28 of the outer tube 22 abuts the cortical bone surface 34 to serve as a stop for the practitioner. This is shown in FIG. 26. FIG. 27 illustrates the inserter and loaded anchor inside the bone hole. While holding the inserter down against the bone surface, the distal end (tip) 20 is retracted to release the anchor 10 inside the hole (FIG. 28). The anchor is now properly placed in the hole with the created pocket, and is ready to be deployed.

Figure 29:
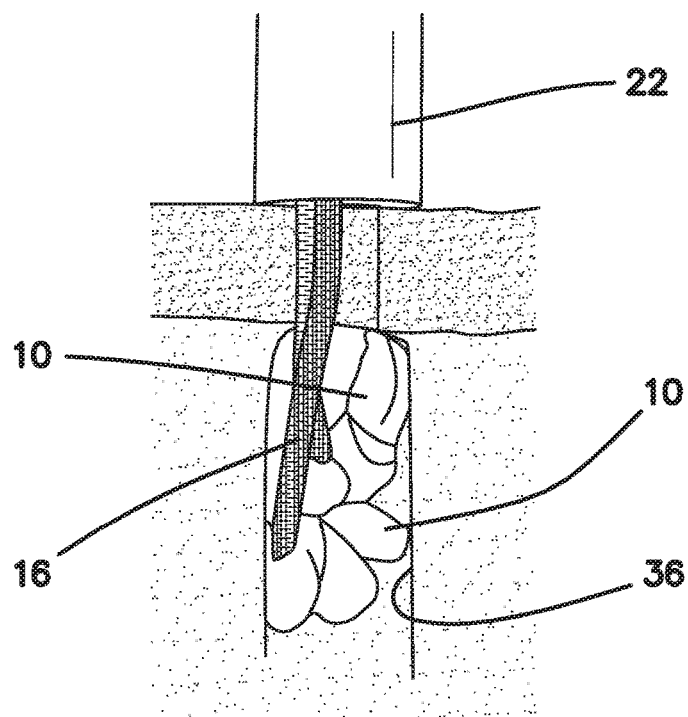
FIG. 29 is a view showing the step applying tension to a suture limb of the bone anchor.
Figure 30:
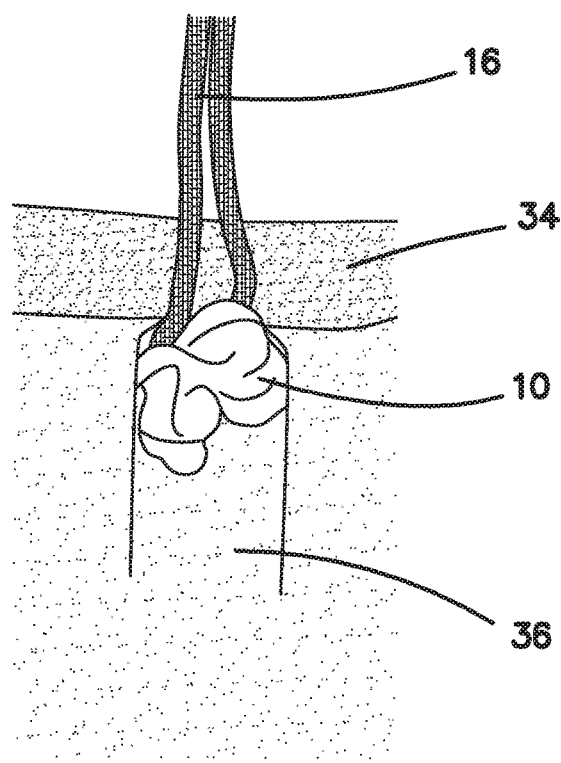
FIG. 30 is a view showing the anchor forming a ball shape beneath the bone surface.

Applying tension on the indicated suture limb 16 causes the anchor 10 to contract vertically, as shown in FIG. 29, and deploys the anchor out to the edges of the pocket 36, as shown. The upper end of the anchor is either caught by the edge of the top lip of the pocket, or stopped by the stopping feature of the inserter while the applied tension is pulling the anchor up. This prevents the anchor from pulling through the hole 32, and forces it to expand circumferentially under the applied tension. FIG. 29 illustrates the anchor in a partially deployed orientation. When completely deployed, as shown in FIG. 30, with the inserter removed from the procedural site, the anchor 10 forms a ball shape beneath the bone surface, filling up the pocket 36 and creating a mechanical blockage through the smaller hole 32 on the bone surface 34. The tensioning suture limb is attachable to soft tissue to be secured to the bone surface 34, for anchoring the soft tissue to the bone.

Accordingly, although exemplary embodiments of the invention has been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of delivering an all-suture suture anchor to a bone site, comprising:
   creating a pre-drilled bone hole in an outer bone surface, the bone hole including a first portion defined by a first internal diameter and a second portion defined by a second internal diameter that is greater than the first internal diameter;
   aligning an anchor inserter with the bone hole, the anchor inserter including an outer sleeve, a distal end portion extending distally beyond a distal end of the outer sleeve, and an internal push rod disposed within the outer sleeve and coupled to the outer sleeve in a fixed longitudinal position, wherein the suture anchor is preloaded into a chamber of the distal end portion;
   positioning the distal end portion of the anchor inserter within the bone hole such that the distal end of the outer sleeve contacts the outer bone surface;
   deploying the suture anchor within the second portion of the bone hole by retracting the distal end portion into the outer sleeve of the anchor inserter; and
   applying tension to a suture limb extending from the suture anchor to expand the suture anchor in the second portion of the bone hole;
   wherein applying tension to the suture limb extending from the suture anchor contracts the suture anchor vertically, thereby causing the suture anchor to expand horizontally in the second portion of the bone hole to a width that is greater than the first internal diameter.

2. The method of claim 1, wherein the width is substantially equal to the second internal diameter.

3. The method of claim 1, wherein the suture anchor expands horizontally by an amount sufficient to cause contact between the suture anchor and a second inner wall of the second portion.

4. The method of claim 1, wherein the suture anchor is fabricated entirely of a suture material and comprises a plurality of suture links, a pre-loaded suture woven through the links, and the suture limb extending from the suture anchor.

5. The method of claim 1, wherein retracting the distal end portion of the anchor inserter causes the internal push rod to push the suture anchor distally out of the anchor inserter.

6. The method of claim 1, wherein creating the bone hole comprises drilling a pilot hole having the first internal diameter.

7. The method of claim 6, wherein creating the bone hole further comprises:
   inserting a drill assembly into the pilot hole to a desired depth;
   moving an actuator to pivot a cutting blade from a retracted position within an outer diameter of an outer sleeve of the drill assembly to an expanded position extending outside of the outer diameter of the outer sleeve; and
   rotating the outer sleeve to enlarge the pilot hole from the first internal diameter to the second internal diameter, thereby forming the first and second portions of the bone hole.

8. The method of claim 7, wherein creating the bone hole further comprises:
   collapsing the cutting blade to the retracted position; and
   removing the drill assembly from the bone hole.

9. A method of delivering an all-suture suture anchor to a bone site, comprising:
   aligning an anchor inserter with a pre-drilled bone hole formed in an outer bone surface, the bone hole including a first portion defined by a first internal diameter and a second portion defined by a second internal diameter that is greater than the first internal diameter, the anchor inserter including an outer sleeve, a distal end portion extending distally beyond a distal end of the outer sleeve, and an internal push rod disposed within the outer sleeve and coupled to the outer sleeve in a fixed longitudinal position such that a spacing between a distal end of the internal push rod and the distal end of the outer sleeve remains constant, wherein the suture anchor is preloaded into a chamber of the distal end portion;
   positioning the distal end portion of the anchor inserter within the bone hole such that the distal end of the outer sleeve contacts the outer bone surface;
   deploying the suture anchor within the second portion of the bone hole by retracting the distal end portion into the outer sleeve of the anchor inserter; and
   applying tension to a suture limb extending from the suture anchor to expand the suture anchor in the second portion of the bone hole.

10. The method of claim 9, wherein the first portion of the bone hole extends from the outer bone surface to a first depth, and the second portion of the bone hole extends from the first depth to a second depth greater than the first depth.

11. The method of claim 10, wherein positioning the distal end portion of the anchor inserter within the bone hole comprises inserting the distal end portion through the first portion of the bone hole and into the second portion of the bone hole.

12. The method of claim 11, wherein the suture anchor expands to a width that is greater than the first diameter, thereby preventing movement of the suture anchor out of the second portion of the bone hole.

13. The method of claim 11, wherein the suture anchor is fabricated entirely of a suture material and comprises a plurality of suture links, a pre-loaded suture woven through the links, and the suture limb extending from the suture anchor.

14. The method of claim 9, wherein retracting the distal end portion into the outer sleeve causes the internal push rod to push the suture anchor distally out of the anchor inserter.

15. The method of claim 14, wherein the internal push rod extends distally beyond the distal end of the outer sleeve.

16. The method of claim 9, wherein the suture anchor expands by an amount sufficient to cause contact between the suture anchor and an internal wall of the bone hole.

17. The method of claim 9, further comprising:
   drilling the bone hole into the outer bone surface at the bone site, the bone hole having the first internal diameter;
   inserting a drill assembly into the bone hole;
   operating the drill assembly to enlarge the bone hole at a desired depth below the outer bone surface, thereby creating the second portion having the second internal diameter; and
   removing the drill assembly from the bone hole.

18. A method of delivering an all-suture suture anchor to a bone site, comprising:
   aligning an anchor inserter with a pre-drilled bone hole formed in an outer bone surface, the bone hole including a first portion defined by a first internal diameter and a second portion defined by a second internal diameter that is greater than the first internal diameter, the anchor inserter including an outer sleeve, a distal end portion extending distally beyond a distal end of the outer sleeve and slidable relative to the outer sleeve, and an internal push rod disposed within the outer sleeve and coupled to the outer sleeve such that a distal end of the internal push rod and the distal end of the outer sleeve are spaced apart by a fixed longitudinal distance during a delivery operation;

positioning the distal end portion of the anchor inserter within the bone hole such that the distal end of the outer sleeve contacts the outer bone surface;

deploying the suture anchor within the second portion of the bone hole by retracting the distal end portion into the outer sleeve of the anchor inserter, thereby causing the internal push rod to push the suture anchor distally out of the anchor inserter; and expanding the suture anchor in the second portion of the bone hole.

\* \* \* \* \*